US008895276B2

(12) United States Patent
Lee et al.

(10) Patent No.: US 8,895,276 B2
(45) Date of Patent: Nov. 25, 2014

(54) MICROORGANISM VARIANTS HAVING HYDROCARBON PRODUCING ABILITY AND METHOD FOR PRODUCING HYDROCARBON USING THE SAME

(75) Inventors: Sang Yup Lee, Daejeon (KR); Yong Jun Choi, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 13/702,920

(22) PCT Filed: Jun. 10, 2011

(86) PCT No.: PCT/KR2011/004289
§ 371 (c)(1),
(2), (4) Date: Feb. 1, 2013

(87) PCT Pub. No.: WO2011/155799
PCT Pub. Date: Dec. 15, 2011

(65) Prior Publication Data
US 2013/0130344 A1    May 23, 2013

(30) Foreign Application Priority Data

Jun. 10, 2010  (KR) .................. 10-2010-0054994

(51) Int. Cl.
*C12P 5/00*    (2006.01)
(Continued)

(52) U.S. Cl.
CPC . *C12P 5/00* (2013.01); *C12N 9/001* (2013.01);
(Continued)

(58) Field of Classification Search
None
See application file for complete search history.

(56) References Cited

U.S. PATENT DOCUMENTS

2009/0084025 A1* 4/2009 Bhatia et al. .................... 44/307
2010/0154293 A1* 6/2010 Hom et al. ....................... 44/385
(Continued)

FOREIGN PATENT DOCUMENTS

CN         101899412 A    12/2010
WO    WO 2007136762 A2 *  11/2007
(Continued)

OTHER PUBLICATIONS

Qi et al., "Metabolic routing towards polyhydroxyalkanoic acid synthesis in recombinant *Escherichia coli* (fadR): inhibition of fatty acid beta-oxidation by acrylic acid", FEMS Microbiology Letters, vol. 167, pp. 89-94, 1998.*

(Continued)

*Primary Examiner* — Rebecca Prouty
*Assistant Examiner* — Richard Ekstrom
(74) *Attorney, Agent, or Firm* — Hultquist, PLLC; Steven J. Hultquist; Mary B. Grant

(57) ABSTRACT

The present invention relates to a microorganism variant having the ability to produce hydrocarbons, including alkane, and a method of producing hydrocarbons, including alkane, using the same, and more particularly, to a microorganism variant obtained by introducing a gene encoding an enzyme converting fatty acyl-acp to free fatty acid, a gene encoding an enzyme converting free fatty acid to fatty acyl-CoA, a gene encoding an enzyme converting fatty acyl-CoA to fatty aldehyde and a gene encoding an enzyme converting fatty aldehyde to alkane into a microorganism improved so as to be suitable for the production of hydrocarbons, including alkane, and a method of producing hydrocarbons, including alkane, using the same. The microorganism variant of the present invention has high potential to be used to improve strains by additional metabolic flux engineering, and thus is useful for the industrial production of hydrocarbons, including alkane.

25 Claims, 4 Drawing Sheets

(51) Int. Cl.

| | |
|---|---|
| C12N 9/02 | (2006.01) |
| C12N 9/18 | (2006.01) |
| C12N 9/88 | (2006.01) |
| C12N 9/00 | (2006.01) |
| C12P 5/02 | (2006.01) |
| C12N 15/52 | (2006.01) |
| C12N 15/70 | (2006.01) |
| C07K 14/245 | (2006.01) |

(52) U.S. Cl.
CPC . *C12N 9/18* (2013.01); *C12N 9/88* (2013.01); *C12N 9/93* (2013.01); *C12P 5/005* (2013.01); *C12P 5/02* (2013.01); *C12P 5/026* (2013.01); *C12N 15/52* (2013.01); *C12N 15/70* (2013.01); *C07K 14/245* (2013.01)
USPC ... 435/166; 435/471; 435/252.3; 435/252.32; 435/252.33

(56) References Cited

U.S. PATENT DOCUMENTS

| | | | |
|---|---|---|---|
| 2010/0235934 A1* | 9/2010 | Friedman et al. | 800/13 |
| 2010/0242345 A1* | 9/2010 | Keasling et al. | 44/388 |
| 2010/0249470 A1* | 9/2010 | Schirmer et al. | 585/14 |
| 2010/0285545 A1* | 11/2010 | Gross et al. | 435/134 |
| 2011/0000125 A1* | 1/2011 | McDaniel et al. | 44/388 |
| 2011/0195469 A1* | 8/2011 | Roessler et al. | 435/155 |
| 2011/0229942 A1* | 9/2011 | Campbell et al. | 435/126 |
| 2013/0078254 A1* | 3/2013 | Bakaletz et al. | 424/139.1 |

FOREIGN PATENT DOCUMENTS

| | | | |
|---|---|---|---|
| WO | WO 2009006430 A1 * | 1/2009 | |
| WO | WO 2009078973 A2 * | 6/2009 | |
| WO | 2009140695 A1 | 11/2009 | |
| WO | WO 2010118410 A1 * | 10/2010 | |
| WO | WO 2012154329 A1 * | 11/2012 | |

OTHER PUBLICATIONS

Cronan et al., "FadR, transcriptional co-ordination of metabolic expediency", Molecular Microbiology, vol. 29, No. 4, pp. 937- 943, 1998.*

DiRusso et al., "Cloning and characterization of a gene (fadR) involved in regulation of fatty acid metabolism in *Escherichia coli*", Journal of Bacteriology, vol. 161, No. 2, pp. 583-588, 1985.*

Datsenko, K., et al., "One-step inactivation of chromosomal genes in *Escherichia coli* K-12 using PCR products", "Proc. Natl. Acad. Sci. USA (PNAS)", Jun. 6, 2000, pp. 6640-6645, vol. 97, No. 12.

Knoll, L., et al., "Use of *Escherichia coli* Strains Containing fad Mutations plus a Triple Plasmid Expression System to Study the Import of Myristate, Its Activation by *Saccharomyces cereuisiae* Acyl-CoA Synthetase, and Its Utilization by *S. cereuisiae* Myristoyl-CoA:Protein N-Myristoyltransferase", "The Journal of Biological Chemistry", Feb. 25, 1993, pp. 4281-4290, vol. 268, No. 6.

Lee, P., et al., "Succinic Acid Production with Reduced By-Product Formation in the Fermentation of *Anaerobiospirillum succiniciproducens* Using Glycerol as a Carbon Source", "Biotechnol. Bioeng.", Jan. 5, 2001, pp. 41-48, vol. 72, No. 1.

Lee, P., et al., "Isolation and characterization of a new succinic acid-producing bacterium, Mannheimia succiniciproducens MBEL55E, from bovine rumen", "Appl. Microbiol. Biotechnol.", Feb. 8, 2002, pp. 663-668, vol. 58, No. 5.

Lee, P., et al., "Batch and continuous cultivation of *Anaerobiospirillum succiniciproducens* for the production of succinic acid from whey", "Applied Microbiology and Biotechnology", Jul. 2000, pp. 23-27, vol. 54, No. 1.

Lee, P., et al., "Batch and continuous cultures of Mannheimia succiniciproducens MBEL55E for the production of succinic acid from whey and corn steep liquor", "Bioprocess. Biosyst. Eng.", Oct. 3, 2003, pp. 63-67, vol. 26, No. 1.

Lee, P., et al., "Biological conversion of wood hydrolysate to succinic acid by *Anaerobiospirillum succiniciproducens*", "Biotechnol. Lett.", Jan. 2003, pp. 111-114, vol. 25, No. 2.

Lennen, R., et al., "A Process for Microbial Hydrocarbon Synthesis: Overproduction of Fatty Acids in *Escherichia coli* and Catalytic Conversion to Alkanes", "Biotechnol. Bioeng.", Jan. 13, 2010, pp. 193-202, vol. 106, No. 2.

Qian, Z., et al., "Metabolic Engineering of *Escherichia coli* for the Production of Putrescine: A Four Carbon Diamine", "Biotechnol. Bioeng.", Aug. 27, 2009, pp. 651-662, vol. 104, No. 4.

Yan, Y., et al., "Engineering metabolic systems for production of advanced fuels", "J Ind Microbiol Biotechnol", Feb. 7, 2009, pp. 471-479, vol. 36.

Dirusso, C., et al., "Bacterial Long Chain Fatty Acid Transport: Gateway to a Fatty Acid-responsive Signaling System", "The Journal of Biological Chemistry", Nov. 26, 2004, pp. 49563-49566, vol. 279, No. 48.

Liu, T., et al., "Quantitative analysis and engineering of fatty acid biosynthesis in *E coli*", "Metabolic Engineering", Feb. 23, 2010, pp. 378-386, vol. 12.

Lu, X., et al., "Overproduction of free fatty acids in *E coli*: Implications for biodiesel production", "Metabolic Engineering", Sep. 9, 2008, pp. 333-339, vol. 10.

Steen, E., et al., "Microbial production of fatty-acid-derived fuels and chemicals from plant biomass", "Nature", Jan. 28, 2010, pp. 559-563, vol. 463.

\* cited by examiner

MICROORGANISM VARIANTS HAVING HYDROCARBON PRODUCING ABILITY AND METHOD FOR PRODUCING HYDROCARBON USING THE SAME

CROSS-REFERENCE TO RELATED APPLICATIONS

This application is a U.S. national phase application under the provisions of 35 U.S.C. §371 of International Patent Application No. PCT/KR2011/004289 filed Jun. 10, 2011, which in turn claims priority of Korean Patent Application No. 10-2010-0054994 filed Jun. 10, 2010. The disclosures of such international patent application and Korean priority patent application are hereby incorporated herein by reference in their respective entireties, for all purposes.

TECHNICAL FIELD

The present invention relates to a microorganism variant having the ability to produce hydrocarbons, including alkane, and a method of producing hydrocarbons, including alkane, using the same, and more particularly, to a microorganism variant obtained by introducing, a gene encoding an enzyme converting fatty acyl-acp to free fatty acid, a gene encoding an enzyme converting free fatty acid to fatty acyl-CoA, a gene encoding an enzyme converting fatty acyl-CoA to fatty aldehyde, and a gene encoding an enzyme converting fatty aldehyde to alkane, into a microorganism improved so as to be suitable for the production of hydrocarbons, including alkane, and a method of producing hydrocarbons, including alkane, using the same.

BACKGROUND ART

In recent years, due to high oil prices and environmental issues, the microbial production of biofuels has attracted a great deal of attention. Also, as biofuels have been considered as alternative fuels to fossil fuels, their market size has increased rapidly. Particularly, alkane has properties suitable for use as fuel, including high energy density, controllable volatility, a sufficient octane number and a low impurity content, and has advantages over ethanol in that it has higher energy efficiency and is more readily miscible with gasoline. In addition, alkane can be used in existing oil pipelines or automobile engines. Thus, if alkane which is the most suitable alternative fuel is produced in large amounts using microorganisms, the import of crude gas can be reduced and the emission of greenhouse gas can be reduced, resulting in environmental effects.

Currently, commercially available gasoline is a linear hydrocarbon compound having 6-10 carbon atoms in one molecule and containing a direct carbon-carbon bond and a straight-chain structure coexisting with a branched-chain structure.

In addition, it contains energy of about 40 MJ per kg, is likely to evaporate at room temperature and atmospheric pressure and has easy and significant inflammability. The most key factor of gasoline is octane number. Some hydrocarbons having a highly branched structure are smoothly burned in the automobile engine, whereas hydrocarbons having an unbranched carbon chain are likely to explode in the cylinder to cause the piston to move intensively. This undesirable explosion causes knocking phenomena in automobiles. As a measure for quantifying this knocking property, the octane number of isooctane (2,2,4-trimethylpentane) which is a high-quality fuel having a highly branched structure is set at 100, and the octane number of heptane which is a low-quality automobile fuel is set at 0. Under this system, a regular grade gasoline has an octane number of about 87. For this reason, it will be important to produce large amounts of highly branched hydrocarbons, which are the key materials in gasoline, such as isooctane.

Usually, the ratio of gasoline in crude oil is only 25%, and this portion is most frequently used as fuel. Thus, in order to increase the production of gasoline in petrochemical plants, a $C_{12}$-$C_{18}$ fraction having a high boiling point is subjected to a cracking process to produce a fraction having a small carbon number and a low boiling point. From this viewpoint, when a fraction of a relatively large carbon number corresponding to kerosene or diesel range fuel is reformed by thermal and catalytic cracking into gasoline in an oil refinery. Studies on the microbial production of hydrocarbons started to increase gradually from studies on the isolation of hydrocarbon-like substances from the cells of marine bacteria and algae due to the development of gas-liquid chromatography. Studies on the microbial production of hydrocarbons can be largely divided into two categories: a method related to intracellular hydrocarbons of microorganism, and a method related to extracellular hydrocarbons of microorganism. With respect to intracellular production, there is a wide variety of systematic groups of microorganisms, which usually show a value of about 0.005-2.69% on a dry mass basis. Strains capable of producing hydrocarbons by this method include cyanobacteria, anaerobic phototrophic bacteria, gram-negative anaerobic sulfate-reducing bacteria, gram-negative facultatively anaerobic bacteria, yeasts, fungi and the like. Each of the strains can produce hydrocarbons of various profiles and shows a unique fraction and predominance. In studies on extracellular production, strains having the ability to produce hydrocarbons include *Desulfovibrio* and *Clostridium*, and strains having the ability to produce isoprene which is a volatile non-methane hydrocarbon include *Actinomycetes*, and strains having the ability to produce ethylene include *Aspergillus clavatus*.

Thus, there have been studies on the optimization of culture conditions in industrially applicable strains capable of producing hydrocarbons, studies on key materials such as hydrocarbon-related genes and enzymes, and studies on metabolic fluxes. However, studies on the analysis of genes and enzymes and the application of metabolic engineering are still insufficient. Thus, a more fundamental approach is required to screen industrially applicable strains, analyze genes associated with the production of target hydrocarbons and isolate metabolic flux-related enzymes from these strains to optimize hydrocarbon production processes, thereby increasing the productivity of hydrocarbons.

Accordingly, the present inventors have made extensive efforts to develop a novel method for microbial production of hydrocarbons, including alkane, and as a result, have constructed a microorganism variant improved so as to suitable for the production of hydrocarbons, including alkane, by constructing a new metabolic pathway that converts fatty acid as a substrate to alkane, and have found that the microorganism variant is useful for the production of alkanes, including octane, nonane and nonene, which are gasoline-range alkanes, as well as pentadecane and heptadecane, thereby completing the present invention.

SUMMARY OF INVENTION

The object of the present invention is to provide a microorganism variant having the ability to produce hydrocarbons, including alkane, and a preparation method thereof.

Another object of the present invention is to provide a method of producing hydrocarbons, including alkane, using the above microorganism variant.

To achieve the above objects, the present invention provides a microorganism variant having the ability to produce hydrocarbons selected from the group consisting of alkanes, alkenes, alkynes, and aromatic hydrocarbons, wherein a gene encoding acyl coenzyme A dehydrogenase and a gene encoding a DNA-binding transcriptional dual regulator are deleted or attenuated, and a gene encoding an enzyme converting fatty acyl-acp to free fatty acid, a gene encoding an enzyme converting free fatty acid to fatty acyl-CoA, a gene encoding an enzyme converting fatty acyl-CoA to fatty aldehyde, and a gene encoding an enzyme converting fatty aldehyde to alkane are introduced or amplified, and a preparation method thereof. The present invention also provides a method for producing hydrocarbons selected from the group consisting of alkanes, alkenes, alkynes, and aromatic hydrocarbons, the method comprising: culturing a microorganism variant having the ability to produce hydrocarbons, thereby producing hydrocarbons selected from the group consisting of alkanes, alkenes, alkynes, and aromatic hydrocarbons; and recovering the hydrocarbons from the culture broth.

DETAILED DESCRIPTION OF THE INVENTION AND PREFERRED EMBODIMENTS

Figure 1:
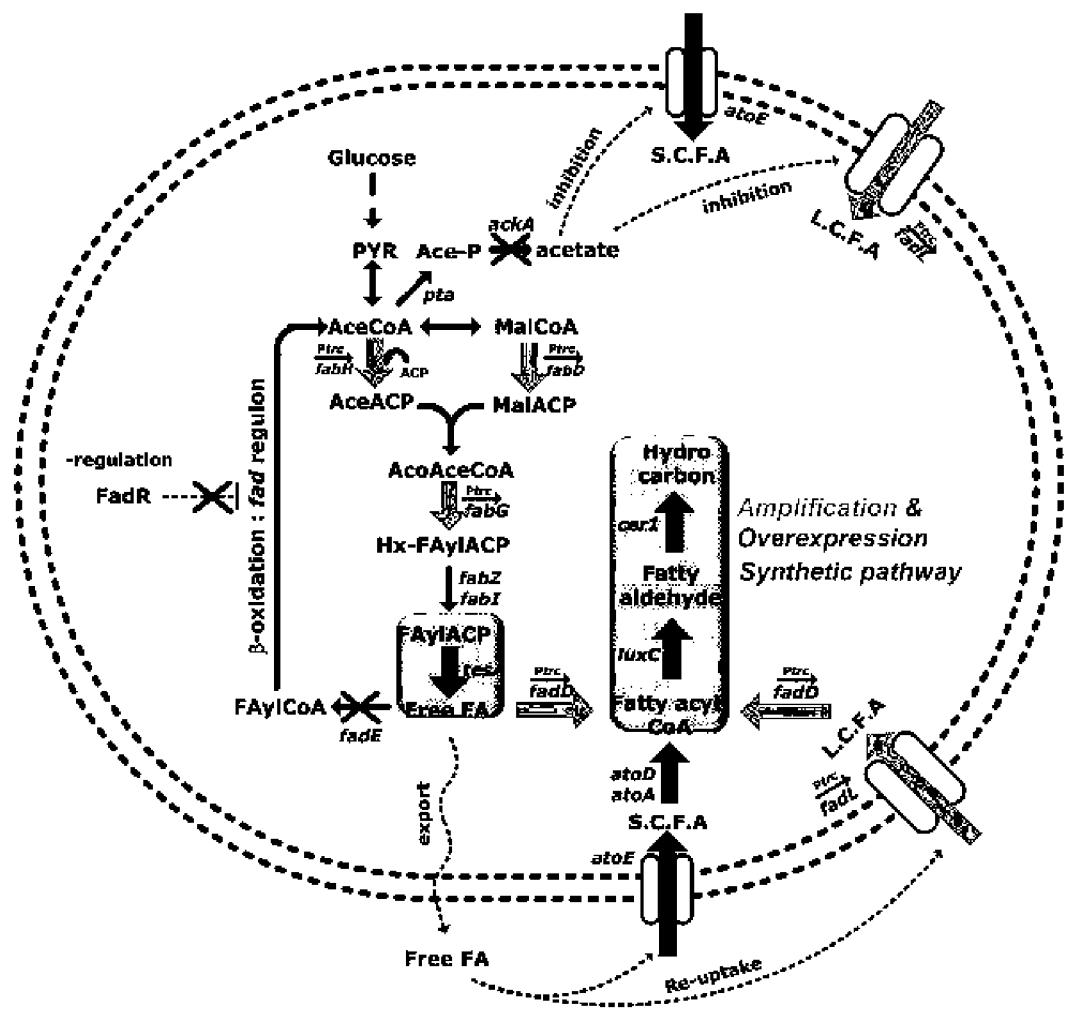
FIG. 1 shows a metabolic pathway for biosynthesizing alkane in a microorganism whose fatty acid metabolism was engineered so as to be suitable for the production of hydrocarbons, including alkane.
Figure 2:
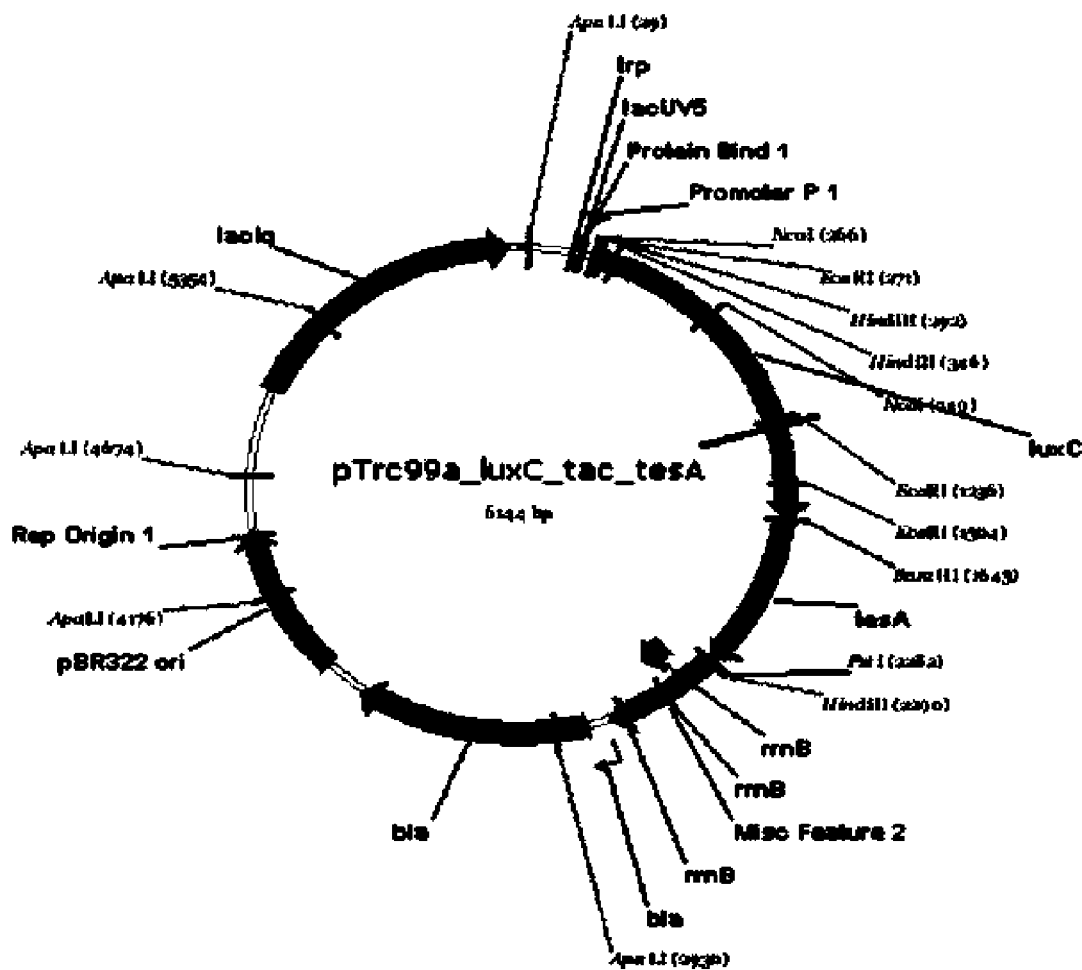
FIG. 2 shows a pTrc99a_luxC_tac_tesA plasmid.
Figure 3:
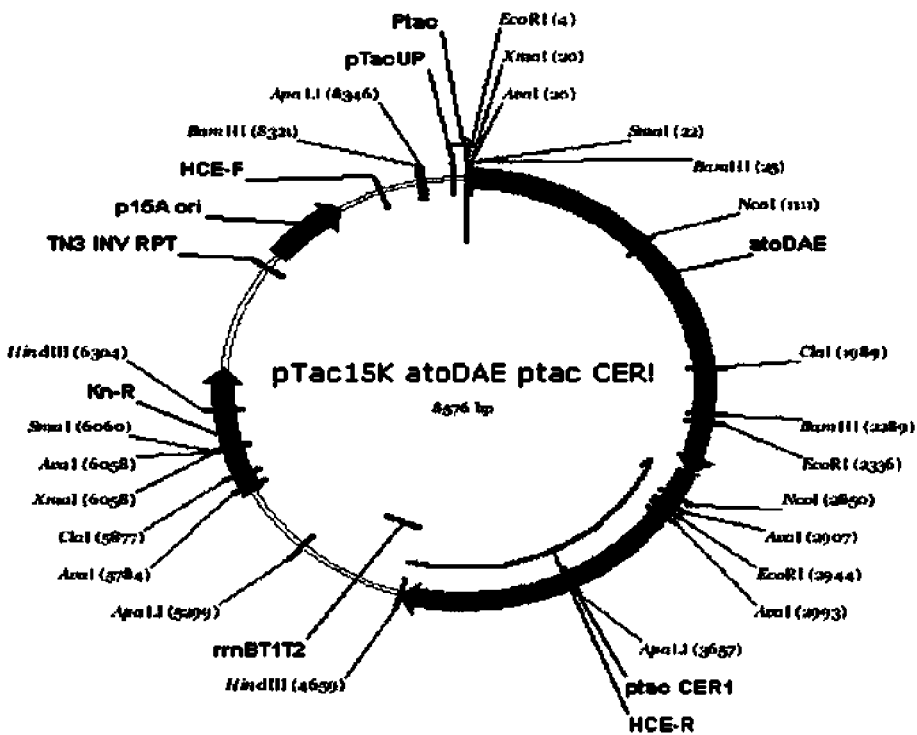
FIG. 3 shows a pTac15k_atoDAE_tac_CER1 plasmid.
Figure 4:
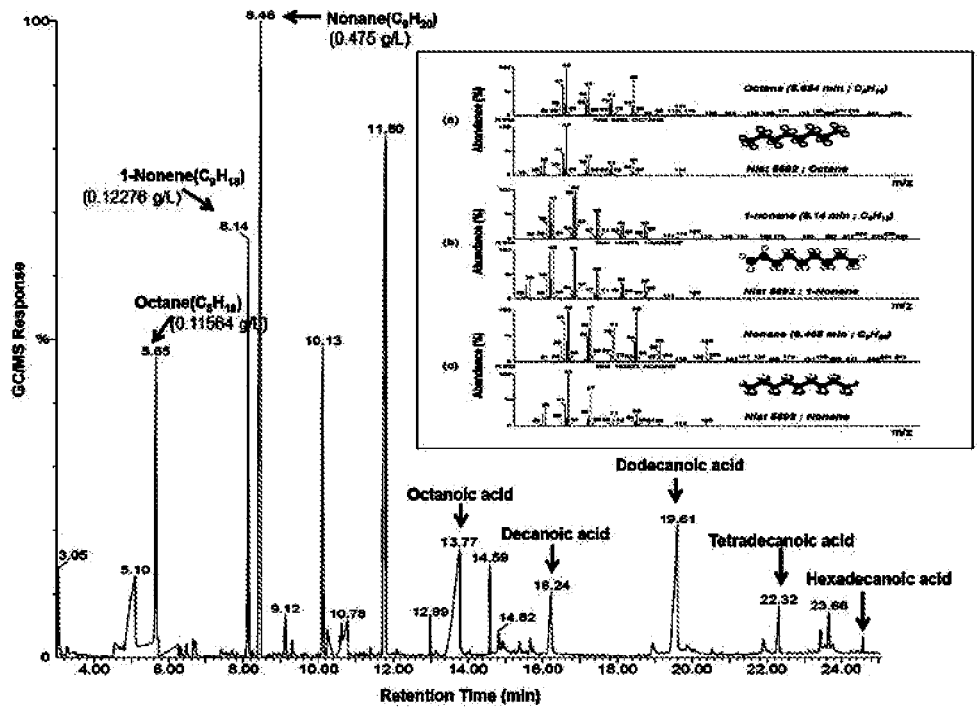
FIG. 4 shows gasoline-range hydrocarbons produced in an improved strain.

Unless defined otherwise, all technical and scientific terms used herein have the same meaning as commonly understood by one of ordinary skill in the art to which the invention pertains. Generally, the nomenclature used herein is well known and commonly employed in the art.

In one aspect, the present invention is directed to a microorganism variant having the ability to produce hydrocarbons selected from the group consisting of alkanes, alkenes, alkynes, and aromatic hydrocarbons, wherein the microorganism variant is constructed by deletion or attenuation of a gene encoding acyl coenzyme A dehydrogenase and a gene encoding a DNA-binding transcriptional dual regulator, and by introduction or amplification of a gene encoding an enzyme converting fatty acyl-acp to free fatty acid, a gene encoding an enzyme converting free fatty acid to fatty acyl-CoA, a gene encoding an enzyme converting fatty acyl-CoA to fatty aldehyde, and a gene encoding an enzyme converting fatty aldehyde to alkane.

In the present invention, in order to increase the ability of the microorganism variant to produce hydrocarbons, including alkane, the native promoter of the gene encoding acyl-CoA synthetase and the attenuator-containing native promoter of the gene encoding the fatty acid outer membrane transporter may further be substituted with a strong promoter in the mutant microorganism, and a gene encoding a short-chain fatty acid outer membrane transporter may further be introduced into the microorganism variant.

In the present invention, in order to increase the ability of the inventive microorganism variant to produce hydrocarbons, including alkane, the native promoter of the fabDHG (fabD: malonyl-CoA-[acyl-carrier-protein] transacylase; fabG: 3-oxoacyl-[acyl-carrier-protein] reductase; fabH: 3-oxoacyl-[acyl-carrier-protein] synthase III) operon and the native promoter of fabA (beta-hydroxydecanoyl thioester dehydrase) may further be substituted with a strong promoter.

Also, the microorganism variant may be constructed by an additional deletion of acetate kinase A encoding gene (ackA).

In the present invention, the microorganism may be selected from the group consisting of bacteria, yeasts, and fungi. Herein, the bacteria may be bacteria having a fatty acid metabolic pathway. Preferably, the bacteria may be selected from the group consisting of *Corynebacterium* sp., *Brevibacterium* sp., and *E. coli*. More preferably, the bacteria may be *E. coli*. Any microorganism capable of using glucose as a carbon source may be used without limitation in the present invention.

In the present invention, the gene encoding acyl coenzyme A dehydrogenase may be fadE, and the gene encoding the DNA-binding transcriptional dual regulator may be fadR. The gene encoding acyl-CoA synthetase may be fadD, and the short-chain fatty acid outer membrane transporter-encoding gene that may further be introduced may be atoE. Meanwhile, the gene encoding the fatty acid outer membrane transporter may be fadL.

In the present invention, the enzyme converting fatty acyl-acp to free fatty acid may be acyl-CoA thioesterase, and the enzyme converting free fatty acid to fatty acyl-CoA may be *Escherichia coli*-derived acetyl-CoA: acetoacetyl-CoA transferase or acyl-coA synthetase.

The enzyme converting fatty acyl-CoA to fatty aldehyde may be *Clostridium kluyveri*-derived fatty acyl-CoA reductase, and the enzyme converting fatty aldehyde to alkane may be *Arabidopsis thaliana* col.-derived fatty aldehyde decarbonylase. In addition, any enzymes may be used in the present invention, as long as they are expressed in host cells to exhibit the same enzymatic activities as the above-described enzymes.

In the present invention, the gene encoding the enzyme converting fatty acyl-acp to free fatty acid may be tesA (acyl-CoA thioesterase-encoding gene), and the gene encoding the enzyme converting free fatty acid to fatty acyl-CoA may be atoDA or fadD (acyl-coA synthetase-encoding gene). Herein, atoDA is composed of atoD (acetyl-CoA: acetoacetyl-CoA transferase alpha subunit) and atoA (acetyl-CoA: acetoacetyl-CoA transferase beta subunit).

The gene encoding the enzyme converting fatty acyl-CoA to fatty aldehyde may be luxC (fatty acyl-CoA reductase-encoding gene), and the gene encoding the enzyme converting fatty aldehyde to alkane may be cer1 (fatty aldehyde decarbonylase 1-encoding gene).

In the present invention, a recombinant vector that is introduced into the microorganism variant may be a vector containing luxC, cer1, tesA or atoDAE gene, which comprises a strong promoter. The recombinant vector may be a pTrc99a_luxC_tac_tesA or pTac15k_atoDAE_tac_CER1 vector, and the strong promoter may be selected from the group consisting of trc promoter, tac promoter, T7 promoter, lac promoter, and trp promoter. In addition, any strong promoter which is generally used in the art may be used without limitation in the present invention.

In another aspect, the present invention is directed to a method for preparing a microorganism variant having the ability to produce hydrocarbons selected from the group consisting of alkanes, alkenes, alkynes, and aromatic hydrocarbons, wherein the microorganism variant is constructed by deletions of a gene encoding acyl coenzyme A dehydrogenase and a gene that encoding a DNA-binding transcriptional dual regulator, and by introduction or amplification of a gene encoding an enzyme converting fatty acyl-acp to free fatty acid, a gene encoding an enzyme converting free fatty acid to fatty acyl-CoA, a gene encoding an enzyme converting fatty acyl-CoA to fatty aldehyde, and a gene encoding an enzyme converting fatty aldehyde to alkane.

In the present invention, in order to increase the ability of the microorganism variant to produce hydrocarbons, including alkane, the native promoter of the gene encoding acyl-CoA synthetase and the attenuator-containing native promoter of the gene encoding the fatty acid outer membrane transporter may further be substituted with a strong promoter in the microorganism variant, and a gene encoding a short-chain fatty acid outer membrane transporter may further be introduced into the microorganism variant.

In the present invention, in order to increase the ability of the inventive microorganism variant to produce hydrocarbons, including alkane, the native promoter of the fabDHG (fabD: malonyl-CoA-[acyl-carrier-protein] transacylase; fabG: 3-oxoacyl-[acyl-carrier-protein] reductase; fabH: 3-oxoacyl-[acyl-carrier-protein] synthase III) operon and the native promoter of fabA (beta-hydroxydecanoyl thioester dehydrase) operon may further be substituted with a strong promoter.

Also, the microorganism variant may be constructed by an additional deletion of acetate kinase A-encoding gene (ackA).

In still another aspect, the present invention is directed to a method for producing hydrocarbons selected from the group consisting of alkanes, alkenes, alkynes, and aromatic hydrocarbons, the method comprising: culturing a microorganism variant having the ability to produce hydrocarbons, thereby producing hydrocarbons selected from the group consisting of alkanes, alkenes, alkynes, and aromatic hydrocarbons; and recovering the hydrocarbons from the culture broth.

In the present invention, a new metabolic pathway that converts fatty acid to alkane was constructed, thereby preparing a microorganism variant having the ability to produce hydrocarbons, including alkane, and whether the prepared microorganism variant can produce hydrocarbons, including alkane, was examined.

The microorganism variant suitable for the production of hydrocarbons, including alkane, is obtained by attenuating or deleting the gene of the enzyme fadE (acyl coenzyme A dehydrogenase) which is the initial step for fatty acid metabolism (converting fatty acyl-CoA to small chain fatty acyl-CoA, acetyl-CoA) and the fadR (DNA-binding transcriptional dual regulator) gene that regulates the genes of the enzymes involved in fatty acid metabolism. Also, it is obtained by substituting the promoter of the fadD (acyl-CoA synthetase) gene converting fatty acid to fatty acyl-CoA and the promoter of the fadL (Long chain fatty acid outer membrane transporter) gene, which involved in the uptake of external fatty acid, with a strong promoter.

It can be inferred that the production of alkane using the microorganism variant according to the present invention is achieved in the following manner. Fatty acyl-acp converted from glucose is converted to free fatty acid by thioesterase, and the free fatty acid is converted to fatty acyl-CoA by acyl-CoA synthetase. The fatty acyl-CoA is converted to fatty aldehyde by fatty acyl-CoA reductase, and the fatty aldehyde is converted to alkane by fatty aldehyde decarbonylase (FIG. 1).

In one Example of the present invention, in order to prepare a microorganism variant suitable for the production of hydrocarbons, including alkane, fadE (acyl coenzyme A dehydrogenase) gene and fadR (DNA-binding transcriptional dual regulator) were deleted from *E. coli* W3110.

The global regulator fadR (DNA-binding transcriptional dual regulator) gene functions to regulate most of genes which are involved in fatty acid metabolism. When a carbon source such as glucose is present, fadR gene strongly represses most of genes which are involved in fatty acid metabolism, whereas when a carbon source such as glucose is not present, fadR can release all the repressed genes and degrade fatty acid. Thus, in the presence of a carbon source such as glucose, the fadR gene strongly represses genes which are involved in fatty acid metabolism, so that fatty acid is not degraded. For this reason, in the present invention, a microorganism was engineered by deleting the fadR gene, so that fatty acid can be degraded even in the presence of glucose.

Because fadE (acyl coenzyme A dehydrogenase) gene is initial step for fatty acid metabolism (converts fatty acyl-CoA to acetyl CoA which is small chain fatty acyl-CoA) a microorganism was engineered by deleting the fadE gene, so that fatty acyl-CoA is not converted to acetyl CoA, but can be converted to fatty acyl aldehyde.

In another Example of the present invention, a ptrc99a_luxC_tac_tesA vector cloned with the gene luxC (fatty acyl CoA reductase-encoding gene) encoding an enzyme converting fatty acyl-CoA to fatty aldehyde, the gene tesA (acyl-CoA thioesterase-encoding gene) encoding an enzyme converting fatty acyl-acp to free fatty acid and a pTac15k_atoDAE_tac_cer1 vector cloned with the operon atoDAE encoding the enzyme converting free fatty acid to fatty acyl-CoA and short-chain fatty acid transporter, respectively and the gene cer1 (fatty aldehyde decarbonlyase 1-encoding gene) encoding an enzyme converting fatty aldehyde to alkane, were constructed. The constructed vectors were introduced into the above mutant organism, thereby constructing a microorganism variant (WERPLD3110+ptrc99a_luxC_tac_tesA+pTac15k_atoDAE_tac_CER1) having the ability to produce alkane.

In still another Example of the present invention, the microorganism variant prepared according to the present invention was cultured, and it was found that the microorganism variant produced octane, nonane and nonene, which gasoline-range alkanes, as well as pentadecane and heptadecane. However, in addition to pentadecane and heptadecane, saturated or unsaturated hydrocarbons can be produced from fatty acids having various carbon structures which can be biosynthesized in microorganisms. Examples of saturated or unsaturated hydrocarbons can be produced from fatty acids having various carbon structures which can be biosynthesized in microorganisms include decane, undecane, tridecane and the like.

In the present invention, culture of the microorganism variant and recovery of hydrocarbons from the culture can be performed using a conventional culture method known in the art. In addition to the specific media and culture methods used in the Examples of the present invention, it is possible to use hydrolysates such as whey or CSL (corn steep liquor) and to use various culture methods such as fed-batch culture or continuous culture (Lee et al., *Bioprocess Biosyst. Eng.*, 26: 63, 2003; Lee et al., *Appl. Microbiol. Biotechnol.*, 58: 663, 2002; Lee et al., *Biotechnol. Lett.*, 25: 111, 2003; Lee et al., *Appl. Microbiol. Biotechnol.*, 54: 23, 2000; Lee et al., *Biotechnol. Bioeng.*, 72: 41, 2001).

As used herein, the term "hydrocarbons" refers to a collection of organic compounds consisting only of carbon and hydrogen. Hydrocarbons are largely divided according to molecular structure into cyclic hydrocarbons and chain-type hydrocarbons. In addition, hydrocarbons are divided into saturated hydrocarbons consisting only of a single bond and unsaturated hydrocarbons containing double bonds or triple bonds.

As used herein, the term "attenuating" is meant to include mutating, replacing or deleting part of the gene of interest, or introducing one or more bases into the gene, so as to reduce the activity of an enzyme, which is expressed by the gene, thereby blocking part, or a substantial part, of the biosynthetic pathway in which the enzyme of the gene is involved.

As used herein, the term "deleting" is meant to include mutating, replacing or deleting part or all of the gene of interest, or introducing one or more bases into the gene, such that the gene is not expressed or does not exhibit enzymatic activity, even though it is expressed, thereby blocking the biosynthetic pathway in which the gene is involved.

Although *E. coli* W3110 was particularly used as a host microorganism in the following examples, it will be obvious to those skilled in the art that other *E. coli* strains, bacteria, yeasts, and fungi may be used without limitation, as long as they can use glucose as a carbon source.

Moreover, although the following examples illustrated introducing genes from specific strains, it will be obvious to those skilled in the art that other genes may also be used without limitation, as long as they are expressed in host cells and show the same activity as the genes used in the examples.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

1-1: Deletion of fadE Gene (Construction of WE3110)

In *E. coli* W3110 (ATTC 39936), the deletion of fadE (acyl coenzyme A dehydrogenase) gene and the removal of antibiotic resistance from *E. coli* W3110 (ATTC 39936) were performed using primers of SEQ ID NOs: 1 and 2 by a one-step inactivation method (Warner et al., PNAS, 97(12):6640-6645, 2000).

[SEQ ID NO: 1]
WfadE k/o F:
5'- atgatgatttgagtattctcgctacggttgtcctgctcggcgcgttgttgtgtaggctgg agctgcttc -3']

[SEQ ID NO: 2]
WfadE k/o R:
5'- actgggcataagccgagaactccagcccgccgtactcttttttgatgatccatatgaatat cctccttag -3'

1-2: Deletion of fadR Gene (Construction of WER3110)

In *E. coli* WE3110 constructed in Example 1-1, the deletion of fadR (DNA-binding transcriptional dual regulator) gene and the removal of antibiotic resistance were performed using primers of SEQ ID NOs: 3 and 4 by a one-step inactivation method (Warner et al., PNAS, 97(12):6640-6645, 2000).

[SEQ ID NO: 3]
WfadR k/o F:
5'- atggtcattaaggcgcaaagcccggcgggtttcgcggaagagtacattatgtgtaggctgg agctgcttc-3'

[SEQ ID NO: 4]
WfadR k/o R:
5'- ccggattggcgaaatagtgacgaccaatacgcgtatacagccctttcatcCATATGAATAT

CCTCCTTAG-3'

1-3: Substitution of Native Promoter of fadD with tac Promoter (Construction of WERPD3110)

In *E. coli* WER3110 constructed in Example 1-2, the native promoter of the fadD gene was replaced with a strong tac promoter in order to make the expression of the fadD gene strong.

Specifically, the native promoter was replaced with tac promoter using the primers of SEQ ID NOs: 5 and 6 in the same manner as the above-described gene removal.

```
                                              [SEQ ID NO: 5]
WfadDpch F:
5'-
gtataatcccggccccgcgagagtacaaacagttgtaactgaataattgcCGCGTCATACA
CATACGATT-3'
                                              [SEQ ID NO: 6]
WfadDpch R:
5'-
ttgatctccgtcggaacgtccgcgggataacggttaagccaaaccttcttCATGGTCTGTT
TCCTGTGTG-3'
```

1-4: Substitution of Attenuator Sequence in Native Promoter of fadL with tac Promoter (Construction of WERPDL3110)

In *E. coli* WERPD3110 constructed in Example 1-3, an attenuator sequence in the fadD promoter, which is involved in transcription regulatory mechanism, was substituted with a strong tac promoter.

For substitution of the attenuator sequence, the attenuator-containing native promoter was substituted with a tac promoter using the primers of SEQ ID NOs: 7 and 8 in the same manner as the above-described gene removal.

```
                                              [SEQ ID NO: 7]
WfadLpch F:
5'-
gaaagtgctgctccagttgttaattctgcaaaatcggataagtgaccgaaCGCGTCATACA
CATACGATT-3'
                                              [SEQ ID NO: 8]
WfadDLpch R:
5'-
actgcgactgcgagagcagactttgtaaacagggttttctggctcatgacCATGGTCTGTT
TCCTGTGTG-3'
```

1-5: Deletion of ackA Gene (Construction of WERAPDL3110)

In *E. coli* WERPDL3110 constructed in Example 1-4, the deletion of ackA (acetate kinase A) gene and the removal of antibiotic resistance were performed using primers of SEQ ID NOs: 9 and 10 by a one-step inactivation method (Warner et al., PNAS, 97(12):6640-6645, 2000).

```
                                              [SEQ ID NO: 9]
WackA k/o F:
5'-
atgtcgagtaagttagtactggttctgaactgcggtagttcttcactgaaTAGGTGACACT
ATAGAACGCG-3'
                                              [SEQ ID NO: 10]
WackA k/o R:
5'-
tgccgtgcgcgccgtaacgacggatgccgtgctctttgtacaggttgtaaTAGTGGATCTG
ATGGGTACC-3'
```

1-6: Substitution of Native Promoter of fabHDG Operon with trc Promoter (Construction of WERAPDLB3110)

In *E. coli* WERAPLD3110 constructed in Example 1-5, the native promoter of fabHDG operon gene was substituted with a strong trc promoter in order to make the expression of the fabHDG operon gene strong.

Specifically, the native promoter was substituted with the trc promoter using the primers of SEQ ID NOs: 11 and 12 in the same manner as the above-described gene removal.

[SEQ ID NO: 11]
WfabHDGpch F:
5'-gtggtggctactgttattaaagcgttggctacaaaagagcctgacgaggcCGCGTCATACACATACGATT-3'

[SEQ ID NO: 12]
WfabHDGpch R:
5'-gtccgcacttgttcgggcagatagctgccagtaccaataatcttcgtataCATGGTCTGTTTCCTGTGTG-3'

1-7: Substitution of Native Promoter of fabA Operon with trc Promoter (Construction of WERAPDLBA3110)

In *E. coli* WERAPLDB3110 constructed in Example 1-6, the native promoter of fabA operon gene was substituted with a strong trc promoter.

Specifically, the native promoter was substituted with the trc promoter using the primers of SEQ ID NOs: 13 and 14 in the same manner as the above-described gene removal.

[SEQ ID NO: 13]
WfabApch F:
5'-accgttttccatggccattacgttggctgaactggtttattccgaactgaCGCGTCATACACATACGATT-3'

[SEQ ID NO: 14]
WfabApch R:
5'-gcgaccagaggcaagaaggtcttcttttgtataggattcgcgtttatctacCATGGTCTGTTTCCTGTGTG-3'

Example 2

2-1: Construction of pTrc99a_luxC Vector

PCR was performed using the chromosomal DNA of a *Clostridium kluyveri* strain (DSMZ, no. 552, German) as a template and the primers of SEQ ID NOs: 15 and 16, thereby constructing a luxC gene fragment encoding fatty acyl CoA reductase.

[SEQ ID NO: 15]
cklluxC F:
5'-TATAGGTACCATGATAGATTGTTATTCATTGGATG-3'

[SEQ ID NO: 16]
cklluxC R:
5'-TATTGGATCCTTAAATATTTAGACTACACCACGTT-3'

Then, the constructed luxC fragment was digested with restriction enzymes (KpnI and BamHI), and a pTrc99a plasmid (Phamacia, Biotech, Uppsala, Sweden) that performs the strong gene expression of a trc promoter was digested with the same restriction enzymes. The digested luxC fragment and plasmid were ligated with each other by T4 DNA ligase, thereby constructing the recombinant plasmid pTrc99a_luxC having a high copy number.

2-2: Construction of pTrc99a_luxC_tac_tesA vector

PCR was performed using the chromosomal DNA of a wild-type *E. coli* (*Escherichia coli* W3110) strain as a template and the primers of SEQ ID NOs: 17 and 18, thereby constructing a tesA gene fragment encoding acyl-CoA thioesterase.

[SEQ ID NO: 17]
tesA F:
5'-TATAGAATTCATGATGAACTTCAACAATGT-3'

[SEQ ID NO: 18]
tesA R:
5'-TATTGAGCTCTTATGAGTCATGATTTACTA-3'

Then, the constructed tesA fragment was digested with restriction enzymes (EcoRI and SacI), and a pTrc99a_luxC plasmid (Phamacia, Biotech, Uppsala, Sweden) that performs the strong gene expression of a trc promoter was digested with the same restriction enzymes. The digested tesA fragment and pTrc99a_luxC plasmid were ligated with each other by T4 DNA ligase, thereby constructing the recombinant plasmid pTrc99a_luxC_tac_tesA having a high copy number.

2-3: Construction of pTac15k_atoDAE_tac_CER1 Vector

Figure 5:
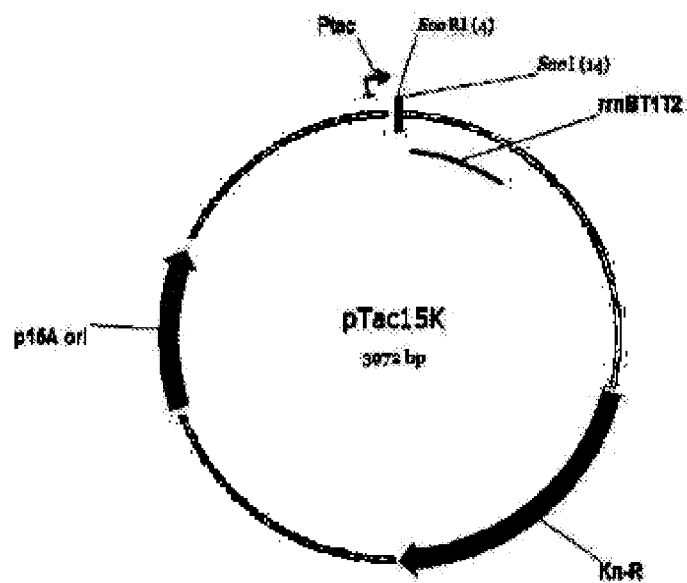
FIG. 5 is a cleavage map of pTac15k.

The trc promoter and transcription terminator regions of pKK223-3 (Pharmacia Biotech., Uppsala, Sweden) were inserted into pACYC177 (NEB, Beverly, Mass., USA), thereby constructing pTac15K. pTac15K is a constitutive expression vector having the structure shown in a cleavage map of FIG. 5. PCR was performed using the chromosomal DNA of Arabidopsis thaliana col. as a template and the primers of SEQ ID NOS: 19 and 20. The resulting CER1 fragment was digested with restriction enzymes (SacI and kpnI) and ligated by T4 DNA ligase into the pTac15k (p15A origin, low copies, KmR; KAISTMBEL stock, tac promoter, 4.0-kb, lap stock)(Zhi-Gang Qian et al., Biotechnology and Bioengineering, 104: 651-654, 2009 and Hiszczyn' ska-Sawicka and Kur, 1997) plasmid digested with the same restriction enzymes, thereby constructing pTac15k_CER1.

Then, PCR was performed using the chromosomal DNA of *E coli* as a template and the primers of SEQ ID NOs: 21 and 22. The resulting atoDAE fragment was digested with restriction enzymes (XbaI and SphI) and ligated by T4 DNA ligase into the pTac15k_CER1 plasmid treated with the same restriction enzymes, thereby constructing pTac15k_atoDAE_tac_CER1. The nucleotide sequences of the primer pairs used in the construction of the vector are as follows:

```
                                          [SEQ ID NO: 19]
CER1F:
5'-TATAGAGCTCATGGCCACAAAACCAGGAGTCCTCACC-3'

[SEQ ID NO: 20]
CER1R:
5'-TATTGGTACCTTAATGATGTGGAAGGAGGAGAGGC-3'

[SEQ ID NO: 21]
atoDAEF:
5'-GCCATCTAGAATGAAAACAAAATTGATGAC-3'

[SEQ ID NO: 22]
atoDAER:
5'-TATTGCATGCTCAGAACAGCGTTAAACCAA-3'
```

Example 3

Measurement of the Ability of Mutant Organism to Produce Alkane

The pTrc99a_luxC_tac_tesA and pTac15k_atoDAE_tac_CER1 plasmids constructed in Examples 2-2 and 2-3 were introduced into WERAPDLBA3110 constructed in Example 1-7 so as to suitable for the production of alkane, and *E. coli* W3110 (ATCC 39936) was used as a control strain. Mutant microorganisms having the ability to produce alkane were selected on LB plate media containing 50 μg/Ml of ampicillin and 30 μg/Ml of kanamycin. The transformed strain was inoculated into 10 Ml of LB medium and pre-cultured at 37° C. for 12 hours. Then, 5 g/L of glucose was added to a 250 Ml flask containing 100 Ml of LB (sterilized at 80° C. or higher), and 1 Ml of the pre-culture broth was inoculated into the flask and cultured at 31° C. for 10 hours. Next, a 5.0-liter fermenter (LiFlus GX, Biotron Inc., Korea) containing 2.0 liter of medium (containing, per liter of distilled water, 20 g glucose, 13.5 g $KH_2PO_4$, 4.0 g $(NH_4)_2 HPO_4$, 1.7 g citric acid, 1.4 g $MgSO_4.7H_2O$, 3 g yeast extract, 10 Ml trace metal solution (per liter of distilled water, 10 g $FeSO_4.7H_2O$, 1.35 g $CaCl_2$, 2.25 g $ZnSO_4.7H_2O$, 0.5 g $MnSO_4.4H_2O$, 1 g $CuSO_4.5H_2O$, 0.106 g $(NH_4)_6 Mo_7O_{24}.4H_2O$, 0.23 g $Na_2B_4O_7.10H_2O$, 35% HCl 10 Ml)) was sterilized at 121° C. for 15 minutes, and then cooled to room temperature. The expression of the introduced or engineered gene was induced using 1 mM IPTG, and the culture medium was maintained at a pH of 6.8 by automatic feeding of 50% (v/v) $NH_4OH$.

The glucose in the culture medium was measured by a glucose analyzer (STAT, Yellow Springs Instrument, Yellow Springs, Ohio, USA), and when the glucose was completely consumed, the cells were recovered, washed once with distilled water, and then dried in a dryer at 100° C. for 24 hours. To the dried cell line, 2 ml of chloroform was added, 1 ml of methanol containing 3% (v/v) $H_2SO_4$ was added thereto, and the mixture was allowed to react at 100° C. for 12 hours. After completion of the reaction, the mixture was cooled was cooled to room temperature, and 1 ml of distilled water was added to the mixture which was then intensively stirred for 5 minutes to separate it into an organic solvent (chloroform) layer and a water layer (aqueous solution). Then, the mixture was centrifuged at 10,000 rpm for 10 minutes, and the organic solvent layer was collected and analyzed by gas chromatography, thereby measuring the production of alkane and fatty acid.

As a result, as can be seen in Table 1 below, in wild-type *E. coli* W3110, no alkane was produced, but in the microorganism variant of the present invention, pentadecane and heptadecane were produced in amounts of 25 mg/L and 40 mg/L, respectively, and octane, nonane and nonene, which are gasoline-range alkanes, were produced in amounts of 0.11564 g/L, 0.475 g/L and 0.12276 g/L, respectively.

Such results suggest that the microorganism variant successfully produces gasoline-range alkanes.

TABLE 1

Production (mg/L) of alkanes in microorganism variant

| Strain | pentadecane (mg/L) | heptadecane (mg/L) | octane (mg/L) | nonane (mg/L) | nonene (mg/L) |
| --- | --- | --- | --- | --- | --- |
| W3110 | ND[1] | ND[1] | ND[1] | ND[1] | ND[1] |
| WERPLD3110 + pTrc99a_luxC_tac_tesA + pTac15k_atoDAE_tac_CER1 | 25 | 40 | 115.64 | 475 | 122.76 |

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

As described above, the present invention provides a microorganism variant obtained by introducing genes, which encode enzymes which are involved in the production of alkane, into a microorganism mutated so as to suitable for the production of hydrocarbons, including alkane. The microorganism variant of the present invention has high potential to be used to improve strains by additional metabolic flux engineering, and thus is useful for the industrial production of hydrocarbons, including alkane.

The invention claimed is:

1. A microorganism variant having the ability to produce alkanes selected from the group consisting of pentadecane, heptadecane, octane, and nonane, wherein a gene encoding acyl coenzyme A dehydrogenase and a fadR gene encoding a DNA-binding transcriptional dual regulator are deleted or attenuated; and a gene encoding an acyl-CoA thioesterase, an atoDA gene encoding an acetyl-CoA: acetoacetyl-CoA transferase, a gene encoding a fatty acyl-CoA reductase, a gene encoding a fatty aldehyde decarbonylase, and an atoE gene encoding a short-chain fatty acid outer membrane transporter are introduced or amplified; and the native promoter of the gene encoding acyl-CoA synthetase and the attenuator-containing native promoter of the gene encoding the fatty acid outer membrane transporter are further substituted with a strong promoter selected from the group consisting of trc promoter, tac promoter, T7 promoter, lac promoter, and trp promoter.

2. The microorganism variant of claim 1, wherein the native promoter of the fabDHG operon and the native promoter of fabA operon are further substituted with a strong promoter in the microorganism variant.

3. The microorganism variant of claim 1, wherein said microorganism variant is constructed by an additional deletion of acetate kinase A-encoding gene.

4. The microorganism variant of claim 1, wherein said microorganism is selected from the group consisting of a bacterium, a yeast, and a fungus.

5. The microorganism variant of claim 4, wherein the said bacterium is a bacterium having the enzymes of a fatty acid metabolic pathway.

6. The microorganism variant of claim 5, wherein said bacterium having the enzymes of a fatty acid metabolic pathway is selected from the group consisting of *Corynebacterium* sp., *Brevibacterium* sp., and *E. coli*.

7. The microorganism variant of claim 1, wherein the gene encoding the acyl coenzyme A dehydrogenase is fadE.

8. The microorganism variant of claim 1, wherein the gene encoding acyl-CoA synthetase is fadD.

9. The microorganism variant of claim 1, wherein the gene encoding the fatty acid outer membrane transporter is fadL.

10. The microorganism variant of claim 1, wherein the gene encoding the acyl-CoA thioesterase is tesA.

11. The microorganism variant of claim 1, wherein the gene encoding the fatty acyl-CoA reductase is luxC.

12. The microorganism variant of claim 1, wherein the gene encoding the fatty aldehyde decarbonylase is cer1.

13. The microorganism variant of claim 2, wherein the strong promoter is selected from the group consisting of trc promoter, tac promoter, T7 promoter, lac promoter, and trp promoter.

14. A mutant *E. coli* having the ability to produce alkanes selected from the group consisting of pentadecane, heptadecane, octane, and nonane, wherein said mutant *E. coli* is constructed by deletion or attenuation of a gene encoding acyl coenzyme A dehydrogenase and a fadR gene encoding a DNA-binding transcriptional dual regulator, and the native promoter of the gene encoding acyl-CoA synthetase and the attenuator-containing native promoter of the gene encoding the fatty acid outer membrane transporter are further substituted with a strong promoter selected from the group consisting of trc promoter, tac promoter, T7 promoter, lac promoter, and trp promoter in the mutant *E. coli*; and wherein said mutant *E. coli* is constructed by introduction or amplification of a gene encoding acyl-CoA thioesterase, an atoDA gene encoding acetyl-CoA: acetoacetyl-CoA transferase, a gene encoding fatty acyl-CoA reductase, a gene encoding fatty aldehyde decarbonylase, and a atoE gene encoding a short-chain fatty acid outer membrane transporter.

15. A mutant *E. coli* having the ability to produce alkanes selected from the group consisting of pentadecane, heptadecane, octane, and nonane, wherein said mutant *E. coli* is constructed by deletions or attenuation of a gene encoding acyl coenzyme A dehydrogenase and a fadR gene encoding a DNA-binding transcriptional dual regulator, and wherein the native promoter of the fabDHG operon and the native promoter of fabA gene are further substituted with a strong promoter selected from the group consisting of trc promoter, tac promoter, T7 promoter, lac promoter, and trp promoter in the mutant *E. coli*, the mutant *E. coli* having introduced or amplified therein a gene encoding acyl-CoA thioesterase, an atoDA gene encoding acetyl-CoA: acetoacetyl-CoA transferase, a gene encoding fatty acyl-CoA reductase, a gene encoding fatty aldehyde decarbonylase, and a atoE gene encoding a short-chain fatty acid outer membrane transporter.

16. A method for preparing a microorganism variant having the ability to produce alkanes selected from the group consisting of pentadecane, heptadecane, octane, and nonane, wherein the microorganism variant is constructed by deletions of a gene encoding acyl coenzyme A dehydrogenase and a fadR gene; and by introduction or amplification of a gene encoding an acyl-CoA thioesterase, an atoDA gene encoding an acetyl-CoA: acetoacetyl-CoA transferase, a gene encoding a fatty acyl-CoA reductase, a gene encoding a fatty aldehyde decarbonylase, and a atoE gene encoding a short-chain fatty acid outer membrane transporter; and by substitution of the native promoter of the gene encoding acyl-CoA synthetase and the attenuator-containing native promoter of the gene encoding the fatty acid outer membrane transporter with a strong promoter selected from the group consisting of trc promoter, tac promoter, T7 promoter, lac promoter, and trp promoter.

17. The method of claim 16, wherein the native promoter of the fabDHG operon and the native promoter of fabA gene are further substituted with a strong promoter.

18. The method of claim 16, which contains an additional deletion of acetate kinase A-encoding gene.

19. The method of claim 16, wherein the microorganism is selected from the group consisting of a bacterium, a yeast, and a fungus.

20. The method of claim 19, wherein said bacterium is a bacterium having the enzymes of a fatty acid metabolic pathway.

21. The method of claim 20, wherein said bacterium having the enzymes of a fatty acid metabolic pathway is selected from the group consisting of *Corynebacterium* sp., *Brevibacterium* sp., and *E. coli*.

22. A method for producing alkanes selected from the group consisting of pentadecane, heptadecane, octane, and nonane, the method comprising: culturing the microorganism variant having the ability to produce alkanes of claim 1 under conditions sufficient to produce alkanes selected from the group consisting of pentadecane, heptadecane, octane, and nonane, thereby producing alkanes selected from the group consisting of pentadecane, heptadecane, octane, and nonane; and recovering the alkanes from the culture broth.

23. A method for producing alkanes selected from the group consisting of pentadecane, heptadecane, octane, and nonane, the method comprising: culturing the mutant *E. coli* having the ability to produce alkanes of claim 14 under conditions sufficient to produce alkanes selected from the group consisting of pentadecane, heptadecane, octane, and nonane, thereby producing alkanes selected from the group consisting of pentadecane, heptadecane, octane, and nonane; and recovering the alkanes from the culture broth.

24. The method of claim 17, wherein the strong promoter is selected from the group consisting of trc promoter, tac promoter, T7 promoter, lac promoter, and trp promoter.

25. A method for producing alkanes selected from the group consisting of pentadecane, heptadecane, octane, and nonane, the method comprising: culturing the mutant *E. coli* having the ability to produce alkanes of claim 15 under conditions sufficient to produce alkanes selected from the group consisting of pentadecane, heptadecane, octane, and nonane, thereby producing alkanes selected from the group consisting of pentadecane, heptadecane, octane, and nonane; and recovering the alkanes from the culture broth.

* * * * *

UNITED STATES PATENT AND TRADEMARK OFFICE
CERTIFICATE OF CORRECTION

PATENT NO. : 8,895,276 B2  Page 1 of 1
APPLICATION NO. : 13/702920
DATED : November 25, 2014
INVENTOR(S) : Lee et al.

It is certified that error appears in the above-identified patent and that said Letters Patent is hereby corrected as shown below:

In the Specification
Column 14, lines 5-10, 15, and 19: Replace "Ml" with -- mℓ --.

Signed and Sealed this
Eighth Day of September, 2015

Michelle K. Lee
*Director of the United States Patent and Trademark Office*

SEQUENCE LISTING

```
<160> NUMBER OF SEQ ID NOS: 22

<210> SEQ ID NO 1
<211> LENGTH: 70
<212> TYPE: DNA
<213> ORGANISM: Artificial
<220> FEATURE:
<223> OTHER INFORMATION: primer

<400> SEQUENCE: 1
atgatgattt tgagtattct cgctacggtt gtcctgctcg gcgcgttgtt gtgtaggctg      60
gagctgcttc                                                            70

<210> SEQ ID NO 2
<211> LENGTH: 70
<212> TYPE: DNA
<213> ORGANISM: Artificial
<220> FEATURE:
<223> OTHER INFORMATION: primer

<400> SEQUENCE: 2
actgggcata agccgagaac tccagcccgc cgtactcttt tttgatgatc catatgaata      60
tcctccttag                                                            70

<210> SEQ ID NO 3
<211> LENGTH: 70
<212> TYPE: DNA
<213> ORGANISM: Artificial
<220> FEATURE:
<223> OTHER INFORMATION: primer

<400> SEQUENCE: 3
atggtcatta aggcgcaaag cccggcgggt ttcgcggaag agtacattat gtgtaggctg      60
gagctgcttc                                                            70

<210> SEQ ID NO 4
<211> LENGTH: 70
<212> TYPE: DNA
<213> ORGANISM: Artificial
<220> FEATURE:
<223> OTHER INFORMATION: primer

<400> SEQUENCE: 4
ccggattggc gaaatagtga cgaccaatac gcgtatacag ccctttcatc catatgaata      60
tcctccttag                                                            70

<210> SEQ ID NO 5
<211> LENGTH: 70
<212> TYPE: DNA
<213> ORGANISM: Artificial
<220> FEATURE:
```

```
<223> OTHER INFORMATION: primer

<400> SEQUENCE: 5
gtataatccc ggccccgcga gagtacaaac agttgtaact gaataattgc cgcgtcatac      60
acatacgatt                                                             70

<210> SEQ ID NO 6
<211> LENGTH: 70
<212> TYPE: DNA
<213> ORGANISM: Artificial
<220> FEATURE:
<223> OTHER INFORMATION: primer

<400> SEQUENCE: 6
ttgatctccg tcggaacgtc cgcgggataa cggttaagcc aaaccttctt catggtctgt      60
ttcctgtgtg                                                             70

<210> SEQ ID NO 7
<211> LENGTH: 70
<212> TYPE: DNA
<213> ORGANISM: Artificial
<220> FEATURE:
<223> OTHER INFORMATION: primer

<400> SEQUENCE: 7
gaaagtgctg ctccagttgt taattctgca aaatcggata agtgaccgaa cgcgtcatac      60
acatacgatt                                                             70

<210> SEQ ID NO 8
<211> LENGTH: 70
<212> TYPE: DNA
<213> ORGANISM: Artificial
<220> FEATURE:
<223> OTHER INFORMATION: primer

<400> SEQUENCE: 8
actgcgactg cgagagcaga ctttgtaaac agggttttct ggctcatgac catggtctgt      60
ttcctgtgtg                                                             70

<210> SEQ ID NO 9
<211> LENGTH: 71
<212> TYPE: DNA
<213> ORGANISM: Artificial
<220> FEATURE:
<223> OTHER INFORMATION: primer

<400> SEQUENCE: 9
atgtcgagta agttagtact ggttctgaac tgcggtagtt cttcactgaa taggtgacac      60
tatagaacgc g                                                           71

<210> SEQ ID NO 10
<211> LENGTH: 70
<212> TYPE: DNA
<213> ORGANISM: Artificial
<220> FEATURE:
<223> OTHER INFORMATION: primer

<400> SEQUENCE: 10
tgccgtgcgc gccgtaacga cggatgccgt gctctttgta caggttgtaa tagtggatct      60
gatgggtacc                                                             70
```

```
<210> SEQ ID NO 11
<211> LENGTH: 70
<212> TYPE: DNA
<213> ORGANISM: Artificial
<220> FEATURE:
<223> OTHER INFORMATION: primer

<400> SEQUENCE: 11
gtggtggcta ctgttattaa agcgttggct acaaaagagc ctgacgaggc cgcgtcatac    60
acatacgatt                                                           70

<210> SEQ ID NO 12
<211> LENGTH: 70
<212> TYPE: DNA
<213> ORGANISM: Artificial
<220> FEATURE:
<223> OTHER INFORMATION: primer

<400> SEQUENCE: 12
gtccgcactt gttcgggcag atagctgcca gtaccaataa tcttcgtata catggtctgt    60
ttcctgtgtg                                                           70

<210> SEQ ID NO 13
<211> LENGTH: 70
<212> TYPE: DNA
<213> ORGANISM: Artificial
<220> FEATURE:
<223> OTHER INFORMATION: primer

<400> SEQUENCE: 13
accgttttcc atggccatta cgttggctga actggtttat tccgaactga cgcgtcatac    60
acatacgatt                                                           70

<210> SEQ ID NO 14
<211> LENGTH: 71
<212> TYPE: DNA
<213> ORGANISM: Artificial
<220> FEATURE:
<223> OTHER INFORMATION: primer

<400> SEQUENCE: 14
gcgaccagag gcaagaaggt cttcttttgt ataggattcg cgtttatcta ccatggtctg    60
tttcctgtgt g                                                         71

<210> SEQ ID NO 15
<211> LENGTH: 35
<212> TYPE: DNA
<213> ORGANISM: Artificial
<220> FEATURE:
<223> OTHER INFORMATION: primer

<400> SEQUENCE: 15
tataggtacc atgatagatt gttattcatt ggatg                               35

<210> SEQ ID NO 16
<211> LENGTH: 35
<212> TYPE: DNA
<213> ORGANISM: Artificial
<220> FEATURE:
<223> OTHER INFORMATION: primer

<400> SEQUENCE: 16
tattggatcc ttaaatattt agactacacc acgtt                               35
```

```
<210> SEQ ID NO 17
<211> LENGTH: 30
<212> TYPE: DNA
<213> ORGANISM: Artificial
<220> FEATURE:
<223> OTHER INFORMATION: primer

<400> SEQUENCE: 17
tatagaattc atgatgaact tcaacaatgt                              30

<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
tattgagctc ttatgagtca tgatttacta                              30

<210> SEQ ID NO 19
<211> LENGTH: 37
<212> TYPE: DNA
<213> ORGANISM: Artificial
<220> FEATURE:
<223> OTHER INFORMATION: primer

<400> SEQUENCE: 19
tatagagctc atggccacaa aaccaggagt cctcacc                      37

<210> SEQ ID NO 20
<211> LENGTH: 35
<212> TYPE: DNA
<213> ORGANISM: Artificial
<220> FEATURE:
<223> OTHER INFORMATION: primer

<400> SEQUENCE: 20
tattggtacc ttaatgatgt ggaaggagga gaggc                        35

<210> SEQ ID NO 21
<211> LENGTH: 30
<212> TYPE: DNA
<213> ORGANISM: Artificial
<220> FEATURE:
<223> OTHER INFORMATION: primer

<400> SEQUENCE: 21
gccatctaga atgaaaacaa aattgatgac                              30

<210> SEQ ID NO 22
<211> LENGTH: 30
<212> TYPE: DNA
<213> ORGANISM: Artificial
<220> FEATURE:
<223> OTHER INFORMATION: primer

<400> SEQUENCE: 22
tattgcatgc tcagaacagc gttaaaccaa                              30
```